United States Patent [19]

Schneider et al.

[11] 4,220,601
[45] Sep. 2, 1980

[54] PROCESS FOR THE CONTINUOUS MANUFACTURE OF 3-NITRO-4-ACETYLAMINO-TOLUENE AND CORRESPONDING APPARATUS

[75] Inventors: Max Schneider, Kelkheim; Lothar Schmitt; Hartmut Heise, both of Bad Soden am Taunus, Fed. Rep. of Germany

[73] Assignee: Hoechst Aktiengesellschaft, Frankfurt am Main, Fed. Rep. of Germany

[21] Appl. No.: 908,360

[22] Filed: May 22, 1978

[30] Foreign Application Priority Data

May 24, 1977 [DE] Fed. Rep. of Germany ....... 2723247

[51] Int. Cl.² .......................................... C07C 103/375
[52] U.S. Cl. ................................ 260/562 R; 422/129; 260/688
[58] Field of Search ............................ 260/688, 562 R

[56] References Cited

U.S. PATENT DOCUMENTS

| | | | |
|---|---|---|---|
| 1,380,185 | 5/1921 | Brewster | 260/688 X |
| 2,128,511 | 8/1938 | Biswell et al. | 260/562 R |
| 2,370,558 | 2/1945 | Mares | 260/688 X |
| 2,737,522 | 3/1956 | Nilsson | 260/688 X |
| 2,813,913 | 11/1957 | Welz et al. | 260/688 X |
| 3,152,117 | 10/1964 | Eijsberg et al. | 422/129 |
| 3,799,993 | 3/1974 | Hill et al. | 260/688 X |
| 3,869,253 | 3/1975 | Lhonore et al. | 260/688 X |
| 3,929,421 | 12/1975 | Werges | 260/561 R |

FOREIGN PATENT DOCUMENTS

40-4812 3/1965 Japan.

*Primary Examiner*—Arthur P. Demers
*Attorney, Agent, or Firm*—Curtis, Morris & Safford

[57] ABSTRACT

3-Nitro-4-acetamino-toluene is obtained by introducing continuously a solution of 4-acetamino-toluene in sulfuric acid and, thereafter, aqueous 40 to 65% (by weight) nitric acid into the circulating reaction mixture. This process is advantageously performed in a device consisting of a closed circuit reactor, two inlets arranged successively in the direction of the product stream, a cooler and an outlet.

6 Claims, 2 Drawing Figures

PROCESS FOR THE CONTINUOUS MANUFACTURE OF 3-NITRO-4-ACETYLAMINO-TOLUENE AND CORRESPONDING APPARATUS

Japanese Patent Application published sub No. 4812/65 describes a process according to which 4-acetaminotoluene in the form of a 25% by weight solution in sulfuric acid is nitrated at room temperature and with thorough intermixing, with a mixture of 66% by weight of nitric acid and 34% by weight of sulfuric acid. In this process, both currents of liquid are introduced into the first one of two directly connected reaction chambers. The product obtained contains however an inadmissibly large amount of by-products especially isomers and oxidation products.

There has now been found a process for the continuous manufacture of 3-nitro-4-acetamino-toluene, by nitration of a solution of 4-acetamino-toluene in sulfuric acid, at room temperature or slightly elevated temperature, with cooling and thorough intermixing, which comprises introducing first the solution of 4-acetaminotoluene in sulfuric acid into the circulating reaction mixture, and subsequently, downstream, a 40 to 65%, preferably 50% by weight, aqueous nitric acid.

Figure 1:
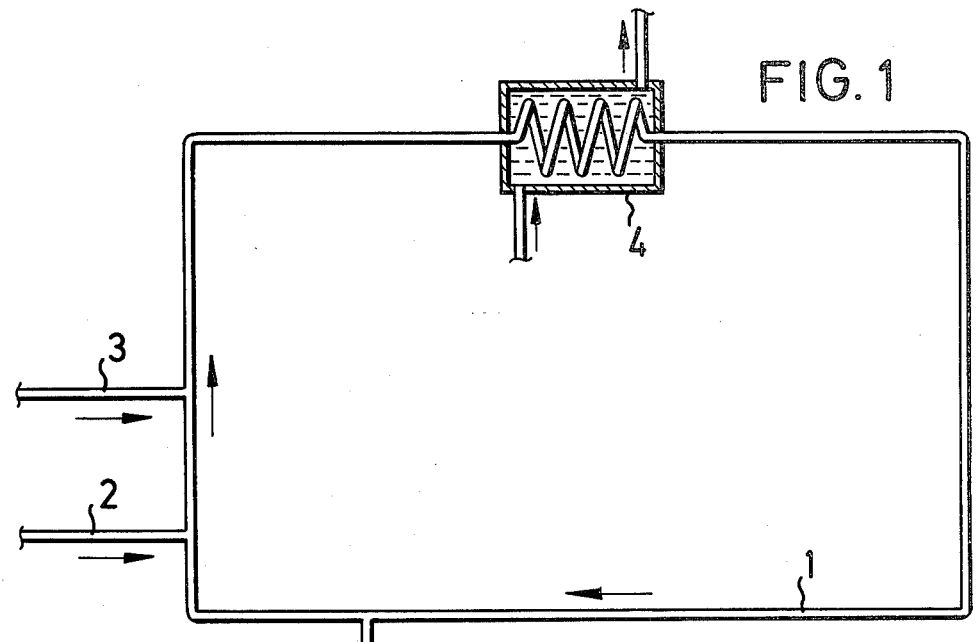

Subject of the present invention is furthermore an apparatus for carrying out the process, which comprises a closed circuit reactor (1) provided with a feeding device (2) for the 4-acetaminotoluene solution, and, downstream, a further feeding device (3) for the aqueous nitric acid, a cooler (4) and an outlet device (5) for the product; these devices being arranged one after the other in the direction of flow (as shown in FIG. 1 of the accompanying drawing).

Figure 2:
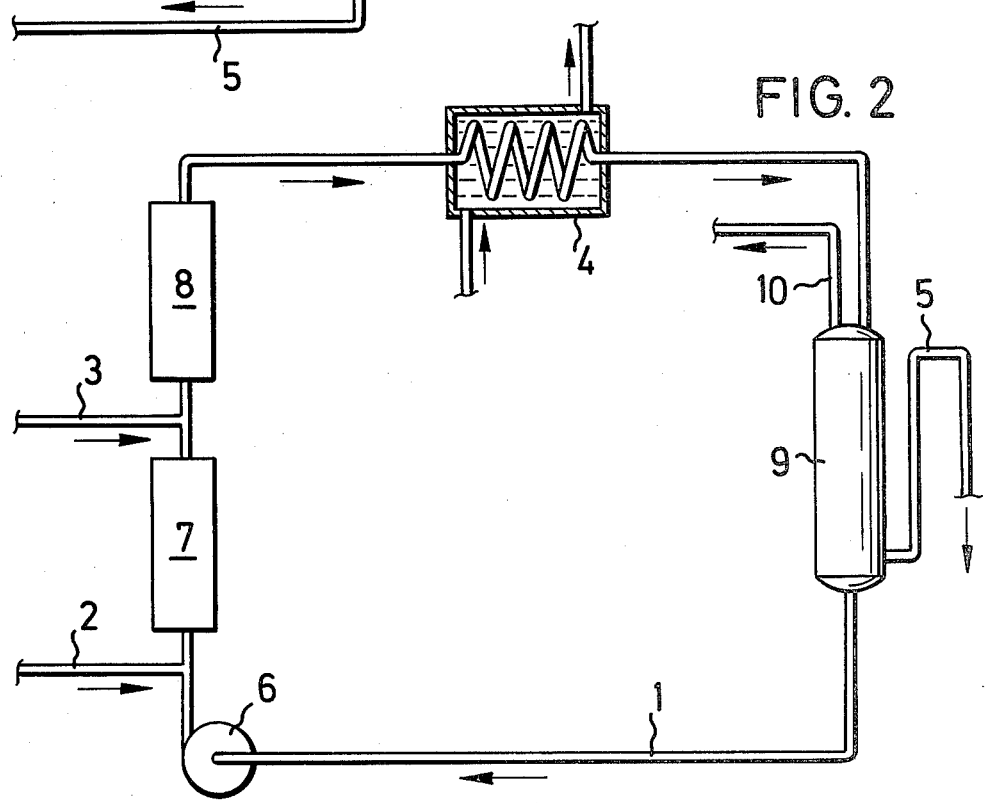

FIG. 2 of the accompanying drawing illustrates a preferred embodiment of the apparatus and process of the invention, which will be explained as follows:

The 4-acetaminotoluene solution in sulfuric acid is introduced into the cooled circulating current in such a manner that thorough intermixing is ensured, which is preferably realized by feeding the above solution through a first inlet opening (2) to the product current conveyed by a circulation pump (6), which current enters subsequently a premixer (7). After homogeneous distribution of the 4-acetaminotoluene, the aqueous nitric acid is fed through a second inlet opening (3) into the circulating current. The reactants are then completely intermixed in the reaction mixture (8), where the nitration reaction begins. The nitration heat is dissipated in the subsequent cooler (4), from where the reaction mixture is forwarded to a buffer vessel (9), where the reaction is completed. This buffer vessel (9) is provided with an exhaust tube (10). Furthermore, a partial product current can be discharged from the buffer vessel (9) via the outlet (5). By dimensioning the buffer vessel (9) accordingly and/or by modifying the amount of charge, the optimum residence time for the corresponding throughput can be adjusted. Further control is made possible by regulating the feed of the components, the ratio of the reactants introduced into the circulating current, the cooling and the circulation rate.

Of course, any other arrangement of the individual elements of this apparatus, or replacement of individual elements by other equivalent means having substantially the same effect is possible. For example, the mixing devices (7) and (8) may be omitted when the reactants are introduced with sufficient turbulence. Furthermore, the buffer vessel (9) may be omitted when the apparatus is dimensioned accordingly, and optionally, the circulating pump (6) may be omitted when the reactants are correspondingly fed in. On the other hand, several mixers, coolers or buffer devices may be provided which are connected in series, i.e., one after the other or in parallel.

The present invention provides a number of advantages as compared to the process of the above Japanese Patent Application: Above all, the process of the invention allows a far better control. The separate feed of the reactants and the improved homogenization with the circulating current prevent undesirable local concentration of the reactants. Furthermore, the large amount of circulating mass in the current, which is a multiple of that of the reactants added, preferably the about 10- to 30-fold amount, is a variable buffer which absorbs undesirable peaks of reaction temperature and concentration. The use of aqueous nitric acid not only eliminates separate preparation of the acid mixture, but also suppresses the formation of undesirable by-products, especially isomers and oxidation products. Furthermore, the apparatus of the invention provides a far better cooling capacity, because the closed circuit system allows the use of highly efficient heat exchangers, for example pipe coolers or surface heat exchangers, which ensure a considerably higher degree of heat transfer than the known process employing the two-chamber apparatus is able to provide. The favorable ratio of heat exchanger at hand to operational volume allows therefore a design saving space and material, thus resulting in high space-time yields and ensuring low investment expenditure. The resulting low specific apparatus volume greatly reduces the safety risks involved in nitration processes.

The following example illustrates the invention. The relation of parts by weight to parts by volume is identical to that of kilogram to liter. Percentages are by weight unless otherwise stated.

EXAMPLE

600 Parts by weight of 4-acetaminotoluene are dissolved in 1000 parts by volume of 96% sulfuric acid. The solution so obtained is fed via the inlet opening (2) into a closed circuit reactor (1) made from stainless steel (according to FIG. 2 of the accompanying drawing). Via the inlet opening (3), 50% aqueous nitric acid is fed in in such a manner that 0.3 part by volume of nitric acid is introduced per part by volume of 4-acetaminotoluene solution. The rates of pump-circulation, feed and cooling are controlled in such a manner that the temperature is maintained between 20° and 35° C.

After precipitation of the discharged reaction product with water, the yield of 3-nitro-4-acetamino-toluene is 89% of the theory.

What is claimed is:

1. A process for the continuous manufacture of 3-nitro-4-acetamino-toluene which comprises the steps of
   first, feeding a solution of 4-acetamino-toluene in sulfuric acid into a cooled circulating reaction mixture having a circulating mass therein in such a manner to cause a homogeneous distribution of the 4-acetamino-toluene in the circulating reaction mixture; and
   second, at a point downstream of the first step, nitrating the 4-acetamino-toluene at a temperature which ranges between room temperature and a slightly elevated temperature by feeding aqueous 40 to 65% by weight nitric acid, in the absence of sulfuric acid, into the circulating reaction mixture containing the homogeneous distribution of the 4-acetamino-toluene in such a manner to cause a thorough intermixing of the aqueous nitric acid and the 4-acetamino-toluene in the circulating reaction mixture.

2. The process, as claimed in claim 1, comprising the steps of first, feeding a solution of 4-acetamino-toluene in sulfuric acid into the circulating reaction mixture;

second, conveying the solution of 4-acetamino-toluene in sulfuric acid and circulating reaction mixture to a premixer;

third, mixing in the premixer the solution of 4-acetamino-toluene in sulfuric acid and circulating reaction mixture to cause a homogeneous distribution of the 4-acetamino-toluene;

fourth, at a point downstream of the third step, feeding aqueous 40–65% by weight nitric acid, in the absence of sulfuric acid, into the circulating reaction mixture containing the homogeneous distribution of the 4-acetamino-toluene;

fifth, conveying the aqueous nitric acid and circulating reaction mixture containing the homogeneous distribution of the 4-acetamino-toluene to a mixer;

sixth, mixing in the mixer the aqueous nitric acid and circulating reaction mixture containing the homogeneous distribution of the 4-acetamino-toluene to cause a thorough intermixing of the aqueous nitric acid and 4-acetamino-toluene and the nitration of the 4-acetamino-toluene at a temperature which ranges between room temperature and a slightly elevated temperature.

3. The process, as claimed in claims 1 or 2 wherein in the first step aqueous nitric acid, about 50% by weight is fed into the circulating reaction mixture.

4. The process, as claimed in claims 1 or 2, wherein the temperature is maintained between 20° and 35° C.

5. The process, as claimed in claims 1 or 2, wherein the solution of 4-acetamino-toluene in sulfuric acid is fed into the circulating reaction mixture with sufficient turbulence to cause a homogeneous distribution of the 4-acetamino-toluene in the circulating reaction mixture; and the aqueous nitric acid is fed into the circulating reaction mixture containing the homogeneous distribution of the 4-acetamino-toluene with sufficient turbulence to cause a thorough intermixing of the aqueous nitric acid and the 4-acetamino-toluene in the circulating reaction mixture.

6. The process, as claimed in claims 1 or 2, wherein the ratio of the weight of the 4-acetamino-toluene and nitric acid fed into the circulating reaction mixture and the weight of the circulating mass in the circulating reaction mixture is between 1:10 and 1:30.

* * * * *